US011577063B2

(12) United States Patent
Kang et al.

(10) Patent No.: US 11,577,063 B2
(45) Date of Patent: *Feb. 14, 2023

(54) SOLUBLE MICRONEEDLE CONTAINING INGREDIENT FOR CONTROLLING RELEASE OF NEUROTRANSMITTERS

(71) Applicant: LG HOUSEHOLD & HEALTH CARE LTD., Seoul (KR)

(72) Inventors: Nae-Gyu Kang, Daejeon (KR); Hyun-Jong Lee, Daejeon (KR); Yun-Hee Chang, Daejeon (KR); Tae-Yoon Kim, Daejeon (KR); Ki-Young Kim, Daejeon (KR); Woo-Sun Shim, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 837 days.

This patent is subject to a terminal disclaimer.

(21) Appl. No.: 16/516,867

(22) Filed: Jul. 19, 2019

(65) Prior Publication Data

US 2019/0336742 A1 Nov. 7, 2019

Related U.S. Application Data

(63) Continuation of application No. 15/566,094, filed as application No. PCT/KR2016/003845 on Apr. 12, 2016, now Pat. No. 10,391,289.

(30) Foreign Application Priority Data

| Apr. 13, 2015 | (KR) | 10-2015-0052043 |
| Apr. 14, 2015 | (KR) | 10-2015-0052575 |
| Oct. 16, 2015 | (KR) | 10-2015-0144855 |
| Nov. 13, 2015 | (KR) | 10-2015-0159978 |

(51) Int. Cl.

| *A61M 37/00* | (2006.01) |
| *A61K 8/34* | (2006.01) |
| *A61K 8/36* | (2006.01) |
| *A61K 9/00* | (2006.01) |
| *A61K 9/70* | (2006.01) |
| *A61Q 19/08* | (2006.01) |

(52) U.S. Cl.
CPC ........... *A61M 37/0015* (2013.01); *A61K 8/34* (2013.01); *A61K 8/36* (2013.01); *A61K 9/0021* (2013.01); *A61K 9/70* (2013.01); *A61M 37/00* (2013.01); *A61Q 19/08* (2013.01); *A61M 2037/0023* (2013.01); *A61M 2037/0046* (2013.01); *A61M 2037/0061* (2013.01); *A61M 2207/00* (2013.01)

(58) Field of Classification Search
CPC .............. A61M 37/0015; A61M 37/00; A61M 2037/0023; A61M 2037/0046; A61M 2037/0061; A61M 2207/00; A61K 8/34; A61K 8/36; A61K 9/0021; A61K 9/70; A61Q 19/08
See application file for complete search history.

(56) References Cited

U.S. PATENT DOCUMENTS

| 8,263,643 | B2 * | 9/2012 | Kweon | A61P 25/00 |
| | | | | 514/685 |
| 10,391,289 | B2 * | 8/2019 | Kang | A61P 43/00 |
| 2004/0052750 | A1 | 3/2004 | Lee et al. | |
| 2004/0147443 | A1 | 7/2004 | Renault | |
| 2007/0148118 | A1 | 6/2007 | Montanari et al. | |
| 2008/0262444 | A1 * | 10/2008 | Takada | A61P 5/50 |
| | | | | 514/777 |
| 2008/0268007 | A1 | 10/2008 | Meng et al. | |
| 2009/0068255 | A1 * | 3/2009 | Yu | A61P 35/00 |
| | | | | 424/59 |
| 2012/0184894 | A1 | 7/2012 | Imran et al. | |
| 2014/0180201 | A1 | 6/2014 | Ding et al. | |
| 2014/0200508 | A1 | 7/2014 | Cohen et al. | |
| 2015/0057604 | A1 | 2/2015 | Arami et al. | |
| 2018/0071208 | A1 | 3/2018 | Shim et al. | |

FOREIGN PATENT DOCUMENTS

| EP | 2 356 980 A2 | 8/2011 |
| JP | 2004-161773 A | 6/2004 |
| KR | 10-0901074 B1 | 6/2009 |
| KR | 10-2010-0041243 A | 4/2010 |
| KR | 10-2010-0094983 A | 8/2010 |
| KR | 10-1041698 B1 | 6/2011 |
| KR | 10-2011-0117667 A | 10/2011 |
| KR | 10-2012-0138235 A | 12/2012 |
| KR | 10-2015-0003745 A | 1/2015 |
| KR | 10-2099326 B1 | 4/2020 |
| WO | WO 2004/006954 A2 | 1/2004 |
| WO | WO 2006/069608 A1 | 7/2006 |

(Continued)

OTHER PUBLICATIONS

Banga, "Transdermal and Intradermal Delivery of Therapeutic Agents," Application of Physical Technologies, Jun. 21, 2011, pp. 53-61.
Al-Qallaf et al., "Transdermal Drug Delivery by Microneedles: Does Skin Metabolism Matter?," International Journal of Chemical Reactor Engineering, vol. 7, Article A69, 2009 (Jan. 1, 2009), pp. 1-23 (27 pages total), XP055513473.
International Search Report for PCT/KR2016/003845 dated Aug. 2, 2016,.
Kaur et al., "Microneedle-assisted Delivery of Verapamil Hydrochloride and Amlodipine Besylate," European Journal of Pharmaceutics and Biopharmaceutics, vol. 86, No. 2, 2014 (Available online Oct. 28, 2013), pp. 284-291, XP028631423, ISSN: 0939-6411, DOI: 10. 1016/J. EJ PB. 2013.10.007.

(Continued)

*Primary Examiner* — Michael P Cohen
(74) *Attorney, Agent, or Firm* — Birch, Stewart, Kolasch & Birch, LLP

(57) ABSTRACT

The present invention relates to a skin administration system capable of improving the efficiency of skin delivery of an ingredient for controlling release of neurotransmitters and, particularly, to a microneedle containing an ingredient for controlling release of neurotransmitters.

10 Claims, 6 Drawing Sheets

(56) References Cited

FOREIGN PATENT DOCUMENTS

| WO | WO 2008/111796 A1 | 9/2008 |
|----|----|----|
| WO | WO 2009/031106 A2 | 3/2009 |
| WO | WO 2009/055860 A1 | 5/2009 |
| WO | WO 2011/154126 A2 | 12/2011 |
| WO | WO 2012/131623 A2 | 10/2012 |
| WO | 10-2012-0138180 A | 12/2012 |
| WO | 10-2013-0135819 A | 12/2013 |
| WO | WO 2014/012075 A2 | 1/2014 |
| WO | WO 2014/041531 A1 | 3/2014 |
| WO | 10-2014-0143416 A | 12/2014 |

OTHER PUBLICATIONS

Kolli et al., "Characterization of Solid Maltose Microneedles and their Use for Transderrnal Delivery," Pharmaceutical Research, vol. 25, No. 1, Jan. 2008 (Published online Jun. 28, 2007), pp. 104-113, XP019579434, ISSN: 1573-904X.

Paleco et al., "Enhancement of the in vitro Penetration of Quercetin through Pig Skin by Combined Microneedles and Lipid Microparticles," International Journal of Pharmaceutics, vol. 472, No. 1, 2014 (Available online Jun. 10, 2014), pp. 206-213, XP029037410, DOI: 10. 1016/J.IPHARM.2014.06.010.

* cited by examiner

SDS-PAGE analysis result of SNARE proteins

Ampelopsin content in pig skin and acceptor solution

Wrinkle improvement test (N=20, p<0.05)

Magnesium gluconate content in pig skin and acceptor solution

Muscle contraction-inhibiting effect of
magnesium gluconate in vitro

Wrinkle improvement test(N=20, p<0.05)

SOLUBLE MICRONEEDLE CONTAINING INGREDIENT FOR CONTROLLING RELEASE OF NEUROTRANSMITTERS

This application is a Continuation of U.S. patent application Ser. No. 15/566,094 filed on Oct. 12, 2017, which is the National Phase of PCT/KR2016/003845 filed Apr. 12, 2016, which claims priority under 35 U.S.C. § 119(a) to Korean Patent Application No. 10-2015-0052043 filed on Apr. 13, 2015, Korean Patent Application No. 10-2015-0159978 filed on Nov. 13, 2015, Korean Patent Application No. 10-2015-0052575 filed on Apr. 14, 2015 and Korean Patent Application No. 10-2015-0144855 filed on Oct. 16, 2015, the disclosures of which are incorporated herein by reference.

TECHNICAL FIELD

The present disclosure relates to a soluble microneedle, more particularly to a system for administering a material modulating the release of a neurotransmitter to the skin.

BACKGROUND ART

Drug delivery through the skin is used in various applications in various forms due to its convenience of use. These drugs passing through the skin are mainly intended to be delivered to the systemic circulatory system, but some drugs such as those for treating atopy and cosmetics for skin whitening or wrinkle improvement, etc. are intended to be delivered to the skin itself. Despite this convenience and functionality, there are many problems in delivering drugs through the skin due to the intrinsic structure of the skin and it is not easy to develop the drugs passing through the skin. The horny layer of the skin consists of a brick structure composed of keratin-rich keratinocytes and a mortar structure composed of ceramides, fatty acids, waxes, etc. filled between the keratinocytes. Because these structures serve as a barrier, the skin has a very low penetrability to materials. Through diffusion, only small molecules with molecular weights of 500 Da or smaller can be delivered into the skin, and only materials having good lipophilicity can pass through the skin.

The release of a neurotransmitter occurs from a synaptic vesicle containing the neurotransmitter located at the nerve ending as the synaptic vesicle is fused with a presynaptic membrane and a passage is formed at the junction. The SNARE protein complex consisting of VAMP (vesicle-associated membrane protein, synaptobrevin), syntaxin 1a and SNAP-25 provides the force that is necessary for the fusion of the synaptic vesicle with the presynaptic membrane. The generation of the release passage of the neurotransmitter by the membrane fusion between the synaptic vesicle and the presynaptic membrane is a result of the action of the t-SNARE complex, which is a complex of the syntaxin 1a protein and the SNAP-25 protein associated with a target membrane, and the v-SNARE complex which is attached to the vesicle. Rearrangement of the lipid bilayer occurs during the membrane fusion. Because biological membranes repel each other strongly, the membranes cannot be fused spontaneously and, thus, a strong external force is required to overcome the repulsive force between the membranes. It is known that this force is provided by the SNARE protein. In other words, the formation of the SNARE complex is critical in exocytosis including the release of a neurotransmitter.

Recently, as it is known that plant-derived polyphenols exert functions similar to that of Botox by modulating the release of neurotransmitters, there have been efforts to use them in the form of applicable cosmetics or in situations where Botox cannot be used. However, because most polyphenols do not have good solubility, the amount that can be included in a cosmetic formulation is limited and, therefore, they are difficult to exhibit efficacy due to very low skin penetrability.

Meanwhile, calcium channel blockers are known to reduce muscle contraction by inhibiting the inflow of calcium, which plays an important role in muscle contraction, into muscle and vascular cells. Facial motion is achieved by contraction of the muscles lying under the skin. Different muscles are used to move different parts of the face.

For the calcium channel blocker to reduce muscle contraction and relax the muscle, the drug should be delivered to the muscular layer. However, it is not easy to deliver the drug to the muscular layer through simple application of cosmetics.

Transdermal injection of the calcium channel blocker may be limited for individuals because of pain. And, oral administration may cause side effects because it affects the whole body.

Although there have been efforts to deliver the calcium channel blocker to the skin by including in cosmetics for improvement of wrinkles and lines, improvement in skin penetration has not been achieved yet.

DISCLOSURE

Technical Problem

The present disclosure is directed to providing a soluble microneedle with a superior skin penetrability.

The present disclosure is directed to providing a soluble microneedle in which an ingredient exhibiting a superior wrinkle-improving effect by blocking the release of neurotransmitters, so that the microneedle is delivered into the skin without pain and the drug is delivered into the skin as the microneedle is dissolved by water in the skin.

According to the present disclosure, the active ingredient is delivered into the skin as the microneedle is dissolved by water in the skin.

According to the present disclosure, the active ingredient delivered into the skin relaxes muscles by blocking the release of neurotransmitters, thereby improving wrinkles and lines on the face without pain.

The present disclosure is directed to providing a system for delivering polyphenols, use of which in general cosmetic compositions has been limited due to poor solubility, into the skin by improving the solubility of the polyphenols.

Technical Solution

In order to solve the problems described above, the present disclosure provides a microneedle containing an ingredient modulating the release of a neurotransmitter. Specifically, the microneedle is a soluble microneedle.

The ingredient modulating the release of a neurotransmitter may be i) a polyphenol or a derivative thereof, ii) a calcium channel blocker or iii) a mixture thereof.

In an exemplary embodiment, the present disclosure provides a microneedle which contains an ingredient modulating the release of a neurotransmitter and has a wrinkle-improving effect. A material forming the microneedle may be soluble or biodegradable in the skin. When the microneedle is applied to the skin, the ingredient modulating the release of a neurotransmitter is released as the microneedle is dissolved or disintegrated. Accordingly, the ingredient modulating the release of a neurotransmitter may be stably delivered into the skin.

In an exemplary embodiment of the present disclosure, the microneedle contains a polyphenol or a derivative thereof.

The inventors of the present disclosure have studied various administration systems but they are limited to be used for application of polyphenols having low solubility included in cosmetic products to the skin. After consistent efforts, the inventors of the present disclosure have surprisingly found out that wrinkle-improving effect can be achieved by effectively reducing the release of a neurotransmitter by including a polyphenol in a microneedle soluble in the skin.

In order to solve the problems described above, the microneedle should be soluble in the skin. To prepare the soluble microneedle, a water-soluble polymer such as hyaluronic acid, sodium carboxymethyl cellulose (Na-CMC), a vinylpyrrolidone-vinyl acetate copolymer, polyvinyl alcohol, polyvinylpyrrolidone, etc., a saccharide such as xylose, sucrose, maltose, lactose, trehalose, etc. or a mixture thereof may be used. In particular, a mixture of hyaluronic acid (or oligo-hyaluronic acid), sodium carboxymethyl cellulose (Na-CMC) and a saccharide (more specifically, trehalose) may be used when considering the skin penetrability, dissolution rate in the skin, etc. of the microneedle. More specifically, a mixture further containing glycerin described below may be used. Specifically, the microneedle according to the present disclosure may further contain, in addition to the above-described ingredients forming the microneedle, a plasticizer, a surfactant, a preservative, an anti-inflammatory agent, etc.

As the plasticizer, for example, a polyol such as ethylene glycol, propylene glycol, dipropylene glycol, butylene glycol, glycerin, etc. may be used alone or in combination.

Specifically, the microneedle of the present disclosure contains a polyphenol exhibiting a wrinkle-improving effect by modulating the release of a neurotransmitter in an amount of 0.01-20 wt %, more specifically 0.1-5 wt %, based on the total weight of a solution for preparing the microneedle.

The microneedle may contain the polyphenol at a high content. The present disclosure may provide a system for delivering a polyphenol to the skin, wherein the amount of the polyphenol delivered to the skin is significantly increased as compared to the general cosmetic composition.

Because the polyphenol has poor solubility, the amount contained in the cosmetic composition is very low. However, because the microneedle of the present disclosure has a very low water content, the polyphenol may be contained in the microneedle at a high content without precipitation to be delivered to the skin.

The polyphenol may be one or more selected from a group consisting of kaempferol, quercetin, myricetin, luteolin, delphinidin, cyanidin, butein, ellagic acid, ampelopsin, hesperidin, aurantinidin, europinidin, pelargonidin, malvidin, peonidin, petunidin, rosinidin and a derivative, specifically one or more selected from a group consisting of ampelopsin, hesperidin or a derivative thereof.

In the present disclosure, the derivative of the polyphenol may be in a free form (free acid or base) or any pharmaceutically acceptable form such as a prodrug, a polymorph, a hydrate, a solvate, a tautomer, a stereoisomer, etc., unless specified otherwise and includes all active forms of the compounds. The microneedle containing the polyphenol according to an exemplary embodiment of the present disclosure can inhibit membrane fusion by inhibiting formation of the SNARE complex and, as a result, can reduce muscle contraction by inhibiting the release of a neurotransmitter, e.g., acetylcholine.

The present disclosure also provides a microneedle patch system for administering (delivering) a polyphenol or a derivative thereof with the microneedle attached.

The microneedle of the present disclosure may be prepared by a method commonly used in the art for preparation of a soluble microneedle and the preparation method is not particularly limited.

For example, the method for preparing the microneedle of the present disclosure may include: (S1) a step of preparing a solution containing an ingredient modulating the release of a neurotransmitter (e.g., a calcium channel blocker, a polyphenol, a derivative thereof or a mixture thereof); (S2) a step of injecting the solution into a microneedle mold; and (S3) a step of drying a microneedle and separating the same from the mold.

The present disclosure also provides a method for administering a polyphenol to the skin with improved solubility and skin penetrability, which uses the microneedle according to the present disclosure.

The present disclosure also provides a use of a microneedle containing a polyphenol which modulates the release of a neurotransmitter and has an effect wrinkle-improving for improving wrinkles.

In an exemplary embodiment of the present disclosure, the present disclosure provides a microneedle which contains a polyphenol and inhibits formation of the SNARE complex.

In another exemplary embodiment of the present disclosure, the present disclosure provides a use of a microneedle containing an ingredient modulating the release of a neurotransmitter for improving skin wrinkles.

In another exemplary embodiment, the present disclosure provides a microneedle which contains a calcium channel blocker and exhibits a wrinkle-improving effect or a facial line-improving effect by relaxing muscles. More specifically, because a material forming the microneedle is soluble in the skin, the microneedle is dissolved or disintegrated when applied to the skin. As a result, the calcium channel blocker is released from the microneedle and can be stably delivered to the skin.

The inventors of the present disclosure have studied various administration systems. After consistent efforts, they have surprisingly found out that a skin wrinkle-improving effect or a lifting effect through improved facial lines can be achieved by effectively reducing the release of a neurotransmitter and, thereby reducing muscle contraction, by including a calcium channel blocker in a microneedle soluble in the skin.

If the calcium channel blocker is contained in a cosmetic formulation such as a cream, a lotion, etc., the desired effect is not achieved sufficiently because of poor skin penetrability. And, injection is not suitable for application at home by individuals. The inventors of the present disclosure have sought to solve these problems and achieve a skin wrinkle-improving effect conveniently without pain. As a result, they have completed the present disclosure.

In order to achieve the object of the present disclosure, the microneedle should be soluble in the skin. To prepare the soluble microneedle, a water-soluble polymer such as hyaluronic acid, sodium carboxymethyl cellulose (Na-CMC), a vinylpyrrolidone-vinyl acetate copolymer, polyvinyl alcohol, polyvinylpyrrolidone, etc., a saccharide such as xylose, sucrose, maltose, lactose, trehalose, etc. or a mixture thereof may be used. In particular, a mixture of hyaluronic acid (or oligo-hyaluronic acid), sodium carboxymethyl cellulose (Na-CMC) and a saccharide (more specifically, trehalose) may be used when considering the skin penetrability, dissolution rate in the skin, etc. of the microneedle. More specifically, a mixture further containing glycerin may be used. Specifically, the microneedle according to the present disclosure may further contain, in addition to the above-described ingredients forming the microneedle, a plasticizer, a surfactant, a preservative, an anti-inflammatory agent, etc.

As the plasticizer, for example, a polyol such as ethylene glycol, propylene glycol, dipropylene glycol, butylene glycol, glycerin, etc. may be used alone or in combination.

Specifically, the microneedle of the present disclosure contains a calcium channel blocker which is capable of modulating the release of a neurotransmitter and modulating muscle contraction in an amount of 0.0001-20 wt %, more specifically 0.001-5 wt %, based on the total weight of a solution for preparing the microneedle.

In the present disclosure, the "calcium channel blocker", also known as a calcium antagonist, refers to a substance which blocks inflow of calcium into muscles and thereby reduces muscle contraction. The calcium channel blocker may be one or more selected from a group consisting of: one or more organometal compound selected from a group consisting of copper gluconate, zinc gluconate, magnesium sulfate, magnesium gluconate and magnesium aspartate; one or more dihydropyridine-based calcium channel blocker selected from a group consisting of amlodipine, lercanidipine, felodipine, nifedipine, nicardipine, isradipine, nisoldipine and a pharmaceutically acceptable salt thereof; a phenylalkylamine-based calcium channel blocker including verapamil; a benzothiazepine-based calcium channel blocker including diltiazem; and an N-type calcium channel blocker selected from a group consisting of gabapentinoid and ziconotide. Any substance that can relax muscles by blocking calcium inflow into a calcium channel may be included without special limitation.

Specifically, the calcium channel blocker may be magnesium gluconate.

The present disclosure also provides a microneedle patch system for administering (delivering) an ingredient modulating the release of a neurotransmitter, specifically a calcium channel blocker, with the microneedle attached.

The present disclosure also provides a method for administering an ingredient modulating the release of a neurotransmitter, specifically a calcium channel blocker, with improved skin penetrability using the microneedle according to the present disclosure.

The present disclosure also provides a microneedle for relaxing facial muscles, which contains an ingredient modulating the release of a neurotransmitter, and a use of the microneedle for relaxing facial muscles.

The use for relaxing facial muscles includes a use for improving wrinkles by reducing muscle contraction, a use for improving facial lines and a use for providing a lifting effect by preventing skin drooping.

In an exemplary embodiment, the present disclosure provides a method for administering an ingredient modulating the release of a neurotransmitter, specifically a calcium channel blocker for improving wrinkles, using the microneedle of the present disclosure.

Advantageous Effects

The present disclosure provides a microneedle having a skin wrinkle-improving effect.

The present disclosure provides a microneedle capable of administering a polyphenol having a wrinkle-improving effect to the skin with improved skin penetrability. The present disclosure also provides a method for administering an ingredient modulating the release of a neurotransmitter using the microneedle.

The present disclosure provides a microneedle having improved skin wrinkle-improving effect or facial line-improving effect.

The present disclosure allows delivery of an active ingredient into the skin without pain by the microneedle.

The present disclosure is capable of improving wrinkles and lines on the face by blocking the calcium channel of neurons and thereby preventing the release of a neurotransmitter and relaxing muscles.

DESCRIPTION OF DRAWINGS

The drawings attached to the specification illustrate specific exemplary embodiments of the present disclosure and are provided for better understanding of the technical idea of the present disclosure together with the foregoing description. Therefore, the present disclosure should not be construed as being limited to the drawings.

MODE FOR DISCLOSURE

Hereinafter, the present disclosure is described in detail through examples in order to help understanding. However, the examples according to the present disclosure can be modified into various different forms and the scope of the present disclosure should not be construed as being limited to the following examples. The examples of the present disclosure are provided to fully explain the present disclosure to those of ordinary skill in the related art.

<Preparation of Soluble Microneedle>

A soluble microneedle was prepared by a solution casting method. It was prepared by casting a solution in a mold, applying vacuum and/or centrifugal force to fill the solution in the hollow cavity of the mold, and then drying the solution. As a material for forming the microneedle, a commonly used synthetic or natural water-soluble polymer was used.

<Preparation of Polyphenol Microneedle for Inhibiting SNARE Formation>

A microneedle having a composition described in Table 1 was prepared. After dissolving hyaluronic acid (Oligo-HA™), sodium carboxymethyl cellulose (Na-CMC) and trehalose in purified water, glycerin, PEG-40 hydrogenated castor oil (HCO-40™) and an ampelopsin solution (ampelopsin 10%, DPG 90%) were added to prepare an ampelopsin solution (DPG: dipropylene glycol). The prepared polyphenol dispersion was cast in a silicone microneedle mold and then filled in the hollow cavity of the mold by centrifuging at 3000 rpm for 10 minutes.

After the filling, the solution was dried in an oven at 70° C. for 3 hours and the resulting microneedle was separated from the silicone mold using an adhesive film. In Table 1, the contents are presented in wt % unit.

Figure 1:
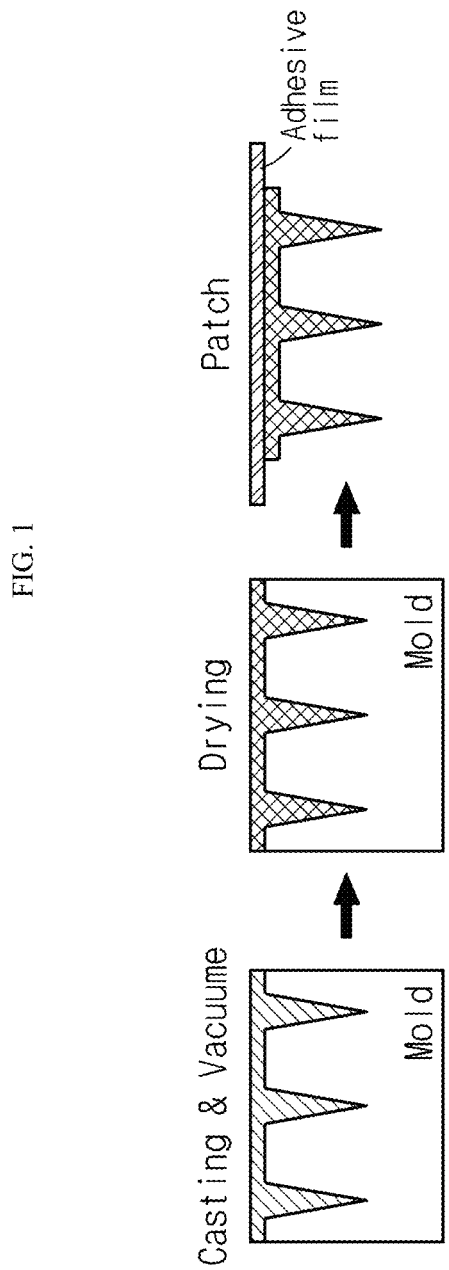
FIG. 1 shows an exemplary embodiment of various methods for preparing a microneedle according to the present disclosure. The soluble microneedle may be prepared by a solution casting method. It may be prepared by casting a solution in a mold, applying vacuum and/or centrifugal force to fill the solution in the hollow cavity of the mold, and then drying the solution. As a material for forming the microneedle, a commonly used synthetic or natural water-soluble polymer may be used.

The preparation process is illustrated in FIG. 1.

TABLE 1

| Ingredients | Contents (wt %) |
|---|---|
| Oligo-HA | 6 |
| Na-CMC | 6 |
| Trehalose | 10 |
| Glycerin | 5 |
| HCO-40 | 0.2 |
| Ampelopsin-DPG solution (10%) | 1.5 |
| Water | To 100 |

<Preparation of Polyphenol Oil-in-Water Cream for Inhibiting SNARE Formation>

For comparison of skin penetration with a polyphenol loaded in the microneedle, a polyphenol was loaded in a commonly used oil-in-water cream as a comparative example.

TABLE 2

| Ingredients | Contents (wt %) |
|---|---|
| $C_{14-22}$ alcohol and $C_{12-20}$ alkyl glucoside (mixture $C_{14-22}$ alcohol:$C_{12-20}$ alkyl glucoside = 80:20, w/w) | 1.5 |
| Glyceryl stearate and PEG-100 stearate (mixture 50:50, w/w) | 1.2 |

TABLE 2-continued

| Ingredients | Contents (wt %) |
|---|---|
| Glyceryl stearate | 0.9 |
| Cetearyl alcohol | 1.5 |
| Polyglyceryl-3 methylglucose distearate | 1.5 |
| Hydrogenated polydecene | 4.5 |
| Cyclohexasiloxane | 3.5 |
| Carbomer | 0.2 |
| Tromethamine | 0.2 |
| Glycerin | 3 |
| DPG | 5 |
| 1,2-Hexanediol | 2 |
| Ampelopsin | 0.5 |
| Purified water | Balance (to 100) |

<Drug Release Behavior>

Figure 2:
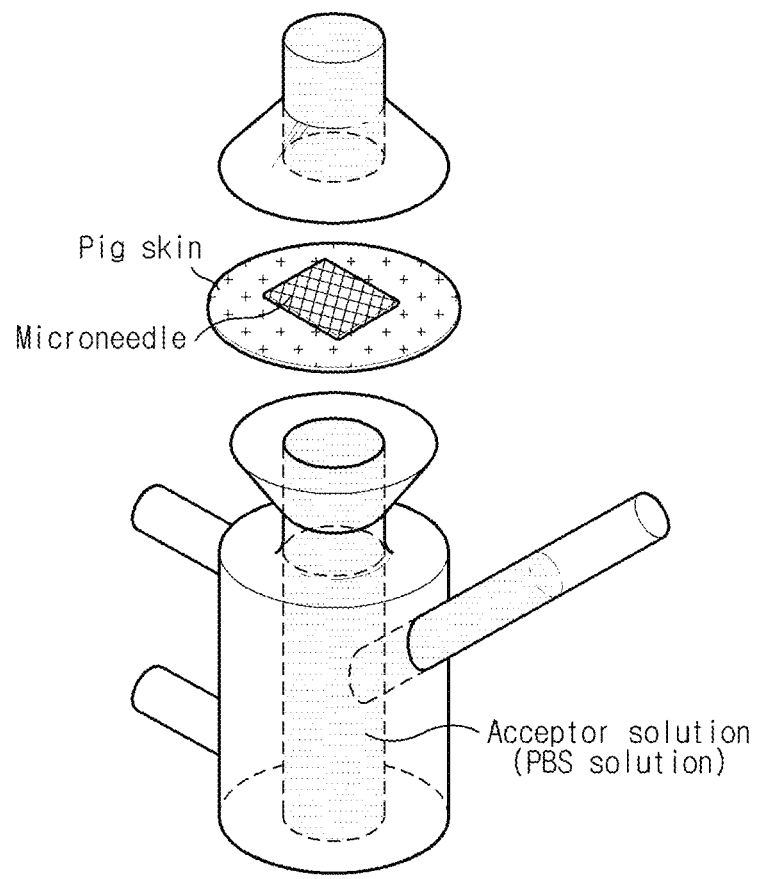
FIG. 2 shows a Franz diffusion cell for testing the release behavior of a drug contained in a microneedle according to the present disclosure.
Figure 3:
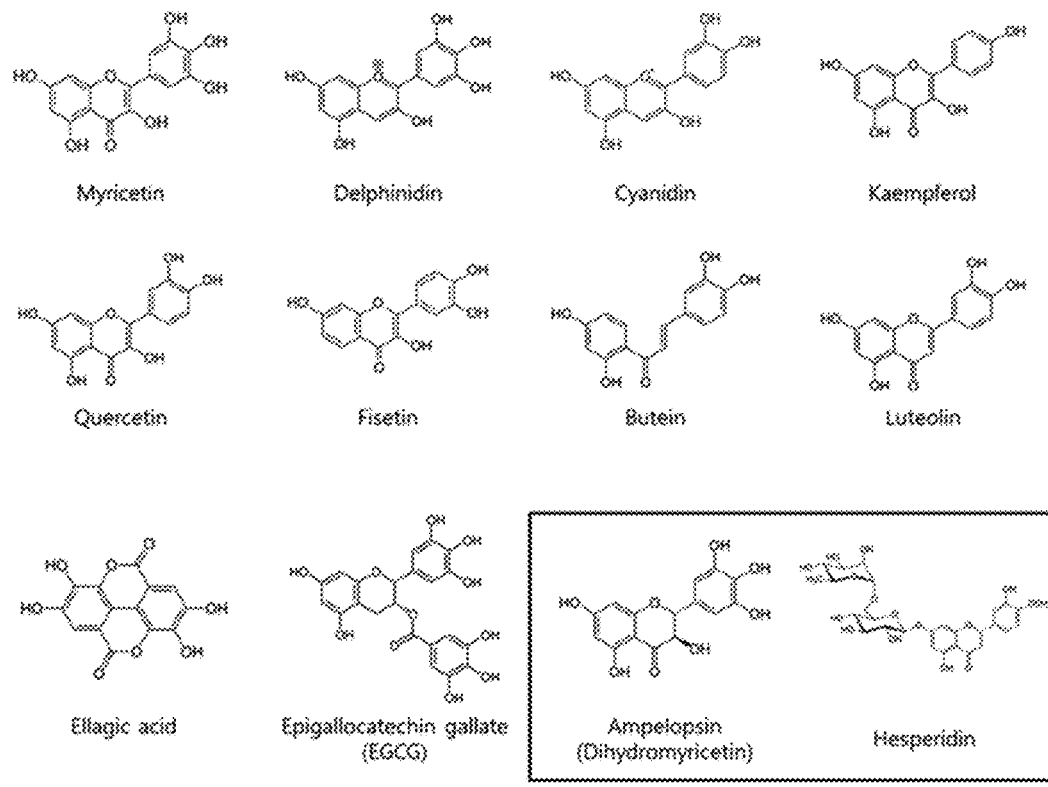
FIG. 3 shows examples of a polyphenol exhibiting an effect similar to that of Botox according to the present disclosure. Myricetin, delphinidin, cyanidin, kaempferol, quercetin, fisetin, butein, luteolin, ellagic acid, EGCG (epigallocatechin gallate), ampelopsin, hesperidin and derivatives thereof may be used.

The release of ampelopsin from the microneedle prepared above was tested using pig skin loaded in a Franz diffusion cell (see FIG. 2). PBS containing 30 wt % DPG was used as an acceptor solution.

The ampelopsin content in the pig skin tissue and in the acceptor solution with time was measured by liquid chromatography using the Franz diffusion cell.

For the ampelopsin-containing cream, the amount passing through the skin was insignificant. In contrast, the ampelopsin-loaded microneedle showed higher skin penetrability than the cream because ampelopsin was delivery directly into the skin by the microneedle.

Figure 5:
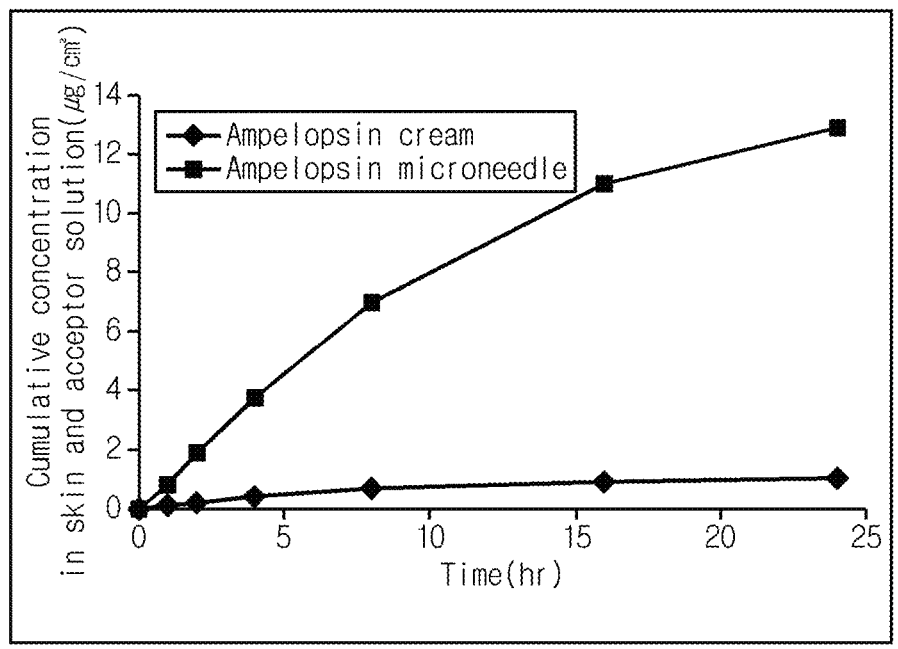
FIG. 5 shows a result of comparing the content of ampelopsin in pig skin and an acceptor solution.

The skin penetration amount was about 13 times or more, with 13 µg or more, for the ampelopsin-loaded microneedle as compared to the ampelopsin-containing cream (about 1 µg). The result is shown in FIG. 5.

<Wrinkle-Improving Effect>

After treating the ampelopsin cream and the ampelopsin-loaded microneedle on eye wrinkles every day for 12 weeks, the degree of wrinkle improvement was evaluated by silicone replica image analysis (N=20).

Figure 6:
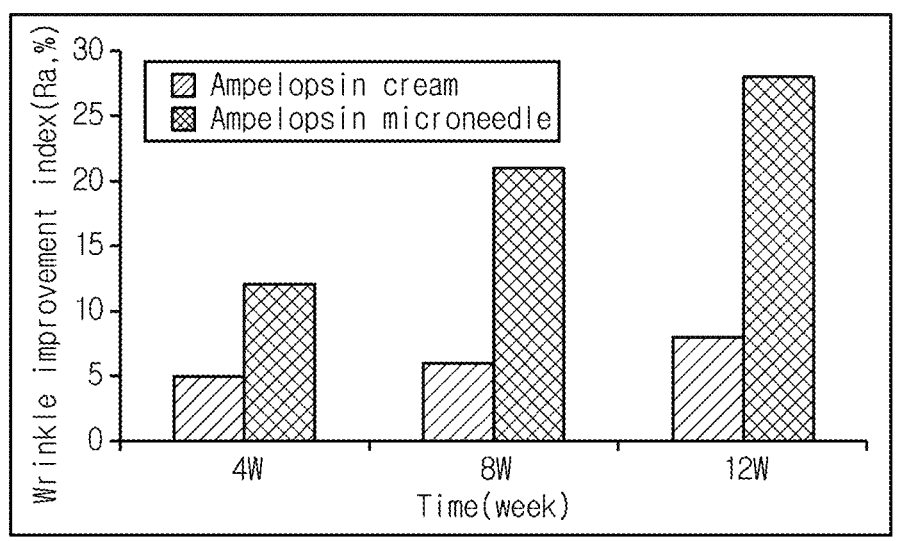
FIG. 6 shows a result of investigating the wrinkle-improving effect of an ampelopsin cream and an ampelopsin microneedle for human.

The ampelopsin-loaded microneedle showed 5 times or better improvement than the ampelopsin cream. The high wrinkle-improving effect is achieved because ampelopsin is effectively delivered into the skin by the microneedle. The result is shown in FIG. 6.

<Inhibition of SNARE Complex Formation>

SDS-PAGE (sodium dodecyl sulfate-polyacrylamide gel electrophoresis) analysis was performed to investigate the inhibition of SNARE complex formation by polyphenols such as ampelopsin, kaempferol, myricetin, etc. It was investigated whether the SNARE complex formed when SNAP25, SynH3 and Vps proteins are mixed at a molar ratio of 1:1:1 was inhibited by the addition of the polyphenol compound at a concentration of 1-50 ppm. After adding the respective proteins dropwise into a 1-mL tube, the polyphenol compound was added and reaction was conducted at room temperature for 30 minutes. Then, it was investigated whether the SNARE complex was formed by electrophoresing on 12% SDS-PAGE.

Figure 4:
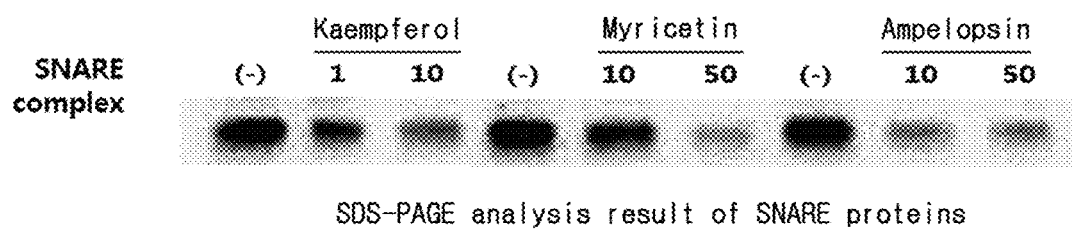
FIG. 4 shows a result of investigating the inhibition of SNARE formation by kaempferol, myricetin and ampelopsin (cell line: C2C12 (muscle cells)+NG108-15 (neuroblasts), concentration: ppm).

It was found out that all of kaempferol, myricetin and ampelopsin effectively inhibit the SNARE complex formation in a concentration-dependent manner. When compared with myricetin, kaempferol and ampelopsin showed better ability of inhibiting SNARE complex formation at low concentrations. The SNARE formation-inhibiting effect of myricetin, ampelopsin (dihydroxymyricetin) and kaempferol at A440 is shown in FIG. 4 (cell line: C2C12 (muscle cells)+NG108-15 (neuroblasts), concentration: ppm).

<Inhibition of Muscle Contraction>

C2C12 cells were cultured in DMEM medium supplemented with 10% fetal calf serum and 1% antibiotic on a plate. Then, neuroblasts were co-cultured additionally on the same plate. When the C2C12 cells began contraction, the number of contractions by the C2C12 cells was measured for 30 seconds. Then, after completely removing the medium and washing 3 times with PBS, the cells were incubated for 2 hours after adding a calf serum-free medium and 50 ppm of the polyphenol compound. Then, the inhibition of muscle contraction was investigated by measuring the number of contractions of the C2C12 cells again for 30 seconds.

Figure 7:
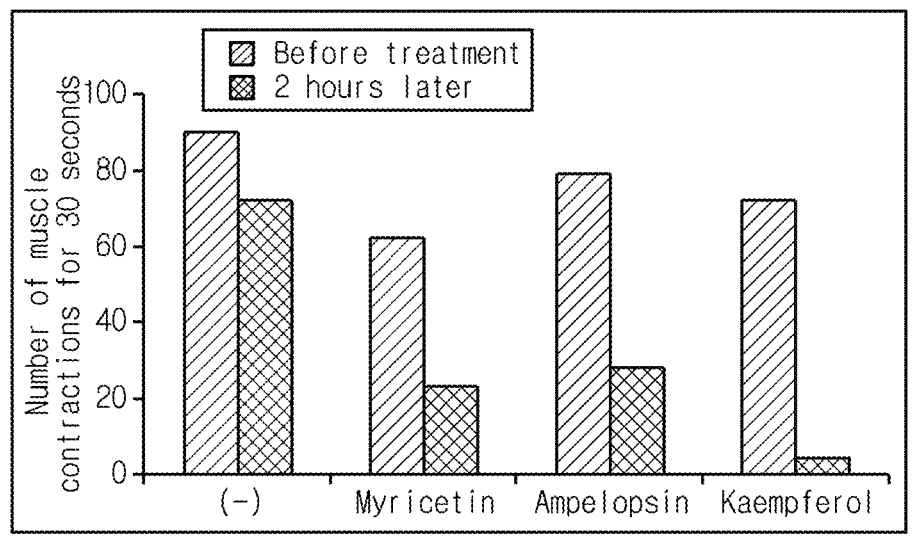
FIG. 7 shows a result of investigating the muscle contraction-inhibiting effect of kaempferol, myricetin and ampelopsin.

It was found out that kaempferol, myricetin and ampelopsin reduce the number of contractions of the C2C12 cells by inhibiting the release of neurotransmitters from the neuroblasts. In particular, ampelopsin and kaempferol showed relatively higher effect of inhibiting the release than myricetin. The result is shown in FIG. 7.

When ampelopsin is prepared into a cosmetic composition, only less than 0.5% (based on 5% PEG-400 and 70% water) of ampelopsin can be contained in the cosmetic composition. In contrast, a microneedle prepared by the method according to the present disclosure may contain ampelopsin up to 5% based on the dry weight of the microneedle. Accordingly, a product containing the polyphenol at high concentration can be prepared.

<Preparation of Soluble Microneedle>

A soluble microneedle was prepared by a solution casting method. It was prepared by casting a solution in a mold, applying vacuum and/or centrifugal force to fill the solution in the hollow cavity of the mold, and then drying the solution.

As a material for forming the microneedle, a commonly used synthetic or natural water-soluble polymer was used.

<Preparation of Magnesium Gluconate-Loaded Soluble Microneedle>

TABLE 3

| Ingredients | Contents (wt %) |
| --- | --- |
| Oligo-HA | 6 |
| Na-CMC | 6 |
| Trehalose | 10 |
| Glycerin | 5 |
| HCO-40 | 0.2 |
| Magnesium gluconate | 0.3 |
| Water | To 100 |

After dissolving Oligo-HA (hyaluronic acid), Na-CMC (sodium carboxymethyl cellulose) and trehalose in purified water, glycerin, HCO-40 and magnesium gluconate were added to prepare a magnesium gluconatesolution (DPG: dipropylene glycol).

The prepared magnesium gluconate dispersion was cast in a silicone microneedle mold and then filled in the hollow cavity of the mold by centrifuging at 3000 rpm for 10 minutes. After the filling, the solution was dried in an oven at 70° C. for 3 hours and the resulting microneedle was separated from the silicone mold using an adhesive film.

<Magnesium Gluconate-Loaded Oil-in-Water Cream>

TABLE 4

| Ingredients | Contents (wt %) |
| --- | --- |
| $C_{14-22}$ alcohol and $C_{12-20}$ alkyl glucoside (mixture $C_{14-22}$ alcohol:$C_{12-20}$ alkyl glucoside = 80:20, w/w) | 1.5 |
| Glyceryl stearate and PEG-100 stearate (mixture 50:50, w/w) | 1.2 |

TABLE 4-continued

| Ingredients | Contents (wt %) |
| --- | --- |
| Glyceryl stearate | 0.9 |
| Cetearyl alcohol | 1.5 |
| Polyglyceryl-3 methylglucose distearate | 1.5 |
| Hydrogenated polydecene | 4.5 |
| Cyclohexasiloxane | 3.5 |
| Carbomer | 0.2 |
| Tromethamine | 0.2 |
| Glycerin | 3 |
| Dipropylene glycol | 5 |
| 1,2-Hexanediol | 2 |
| Magnesium gluconate | 1 |
| Purified water | Balance (to 100) |

For comparison of skin penetration with magnesium gluconate loaded in the microneedle, magnesium gluconate was loaded in a commonly used oil-in-water cream as a comparative example.

<Drug Release Behavior>

The content of magnesium gluconate in the pig skin tissue and in the acceptor solution with time was measured by liquid chromatography using the Franz diffusion cell. After applying the magnesium gluconate cream on the pig skin or attaching the magnesium gluconate-loaded microneedle, the penetration amount of magnesium gluconate into the skin with time was compared.

Figure 8:
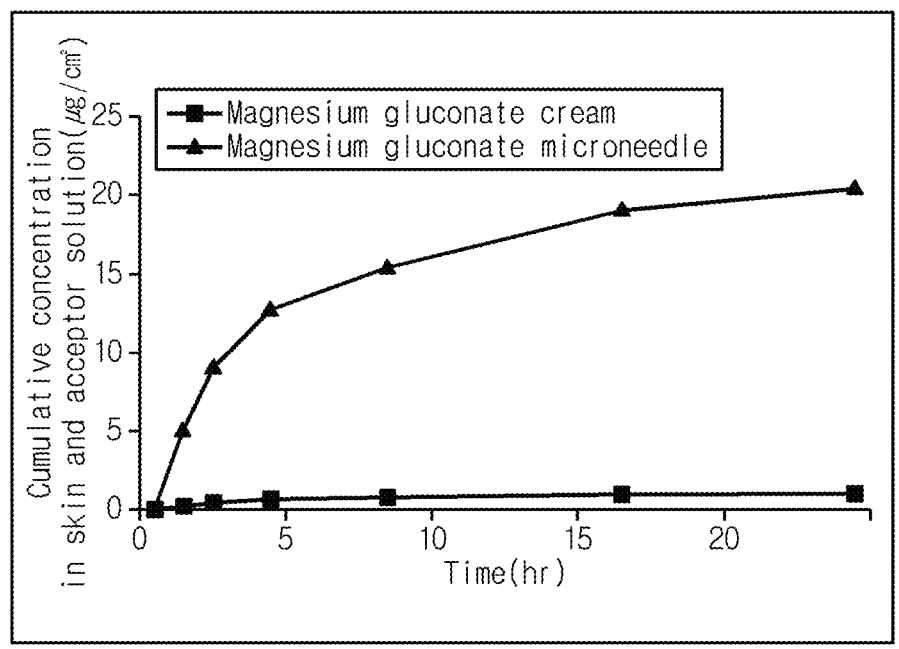
FIG. 8 shows a result of investigating the content of magnesium gluconate in pig skin and an acceptor solution for a magnesium gluconate cream and a magnesium gluconate microneedle.

For the magnesium gluconate-containing cream, the amount passing through the skin was insignificant with about 1 μg or less. In contrast, the skin penetration amount was about 20 times or more, with about 20 μg or more, for the magnesium gluconate-loaded microneedle as compared to the cream because magnesium gluconate was delivery directly into the skin by the microneedle. The result is shown in FIG. 8.

<Inhibition of Muscle Contraction In Vitro>

Figure 9:
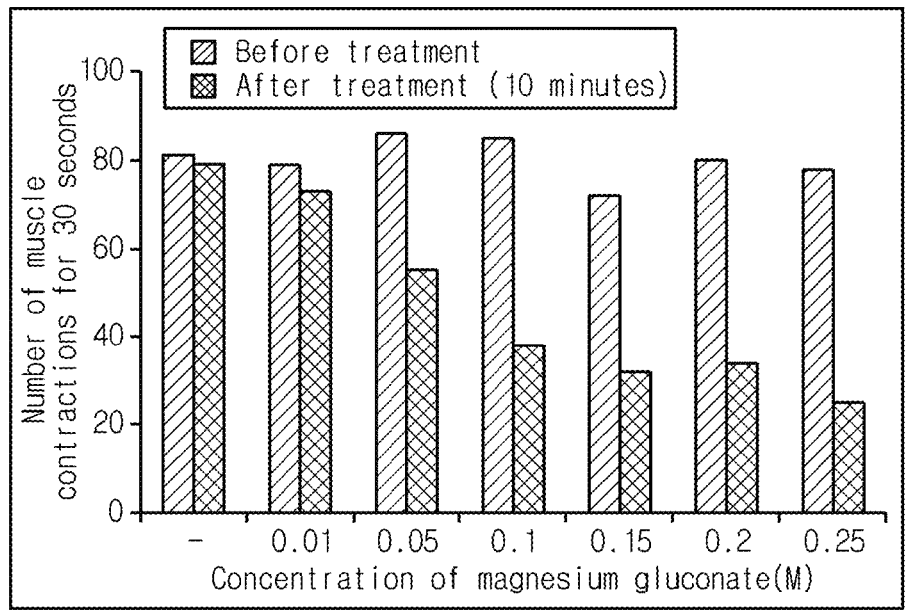
FIG. 9 shows a result of measuring the muscle contraction-inhibiting effect of magnesium gluconate in vitro. After co-culturing muscle cells and neuroblasts in vitro and treating with magnesium gluconate at various concentrations, decrease in the number of muscle contractions was observed 10 minutes later.

As can be seen from FIG. 9, the treatment with magnesium gluconate resulted in significant decrease in the number of muscle contractions as the concentration of magnesium gluconate was increased.

<Wrinkle-Improving Effect>

After treating the magnesium gluconate cream and the magnesium gluconate-loaded microneedle on eye wrinkles every day for 12 weeks, the degree of wrinkle improvement was evaluated by silicone replica image analysis (N=20).

Figure 10:
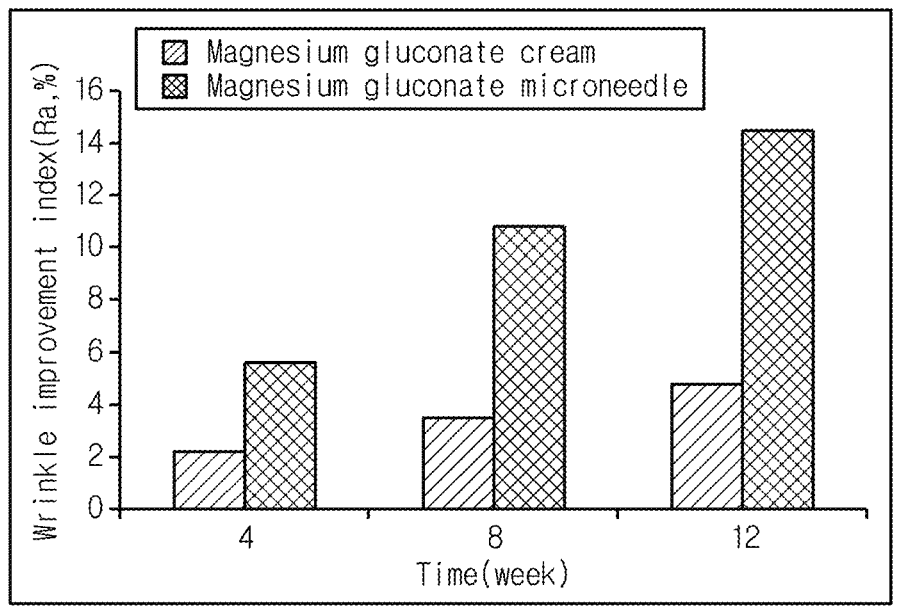
FIG. 10 shows the wrinkle improvement indices of a magnesium gluconate cream and a magnesium gluconate microneedle.

As can be seen from FIG. 10, the magnesium gluconate-loaded microneedle showed 2-3 times or better improvement than the magnesium gluconate cream. The high wrinkle-improving effect is achieved because magnesium gluconate is effectively delivered into the skin by the microneedle.

INDUSTRIAL APPLICABILITY

The present disclosure can be used in cosmetic and pharmaceutical applications for improving skin wrinkles.

The microneedle of the present disclosure may provide a superior effect of reducing skin wrinkles.

What is claimed is:

1. A microneedle comprising an ingredient modulating the release of a neurotransmitter,
    wherein the ingredient modulating the release of a neurotransmitter is one or more polyphenol or derivative thereof selected from the group consisting of ampelopsin, aurantinidin, europinidin, pelargonidin, malvidin, peonidin, petunidin, rosinidin and derivatives thereof.

2. The microneedle according to claim 1, wherein the microneedle comprises 0.01-10 wt % of the polyphenol or derivative thereof based on the total weight of the microneedle.

3. The microneedle according to claim 1, wherein the microneedle is soluble in the skin.

4. The microneedle according to claim 1, wherein a material forming the microneedle comprises hyaluronic acid, sodium carboxymethyl cellulose (Na-CMC), a vinylpyrrolidone-vinyl acetate copolymer, polyvinyl alcohol, polyvinylpyrrolidone, a saccharide or a mixture thereof.

5. The microneedle according to claim 4, wherein the microneedle further comprises a plasticizer in addition to the material forming the microneedle.

6. A microneedle for improving skin wrinkles, which comprise the microneedle according to claim 1.

7. The microneedle according to claim 1, wherein application of the microneedle to a skin improves skin wrinkles.

8. The microneedle according to claim 7, wherein the application of the microneedle improves skin wrinkles by inhibiting muscle contraction.

9. A method for improving skin wrinkles, comprising:
    applying the microneedle according to claim 1 to a subject in need thereof; and
    thereby administering the ingredient modulating the release of a neurotransmitter into the skin.

10. The method according to claim 9, wherein the ingredient modulating the release of a neurotransmitter inhibits muscle contraction, and thereby improving skin wrinkles.

* * * * *